United States Patent [19]

Shiomi et al.

[11] Patent Number: 4,980,042

[45] Date of Patent: Dec. 25, 1990

[54] OXYGEN SENSOR AND METHOD OF MAKING IT

[75] Inventors: Haruhisa Shiomi, Kyoto; Toshihiko Aoyama, Aichi; Yoshitake Kawachi, Aichi; Ken Minoha, Aichi, all of Japan

[73] Assignee: NGK Spark Plug Co., Ltd., Aichi, Japan

[21] Appl. No.: 432,444

[22] Filed: Nov. 6, 1989

Related U.S. Application Data

[63] Continuation-in-part of Ser. No. 196,185, May 16, 1988, abandoned, and a continuation-in-part of Ser. No. 282,980, Nov. 28, 1988, abandoned, which is a continuation of Ser. No. 29,560, Mar. 24, 1987, abandoned.

[30] Foreign Application Priority Data

Mar. 24, 1986 [JP] Japan .................................. 61-66663
Aug. 11, 1987 [JP] Japan ................................ 62-200334

[51] Int. Cl.$^5$ ......................................... G01N 27/409
[52] U.S. Cl. .................................. 204/427; 427/126.3
[58] Field of Search ................ 204/427, 428, 429, 1 S; 427/126.3

[56] References Cited

U.S. PATENT DOCUMENTS 4,455,214 6/1984 Isenberg ............................... 204/428

FOREIGN PATENT DOCUMENTS

272649 12/1986 Japan .

Primary Examiner—G. L. Kaplan
Attorney, Agent, or Firm—Sughrue, Mion, Zinn, Macpeak & Seas

[57] ABSTRACT

An oxygen sensor comprising a hollow cylindrical member closed at one end but open at the other to admit a reference gas. There is at least one radial through-hole in the hollow cylindrical member. An oxygen-ion conductive solid electrolyte later has at least one pair of electrodes on its opposite sides. The electrolyte layer is wrapped around the hollow cylindrical member with the electrode on its inner side facing the through hole. In other embodiments, an oxygen sensor is provided which is very insensitive to the direction of flow of the gas to be analyzed. The electrodes of the sensor are spaced at substantially equal intervals on the circumference of a cylindrical solid electrolyte layer in registry with through-holes formed in a hollow tubular member surrounded by the electrolyte layer. A heating unit may be formed on either the inner or outer surface of the solid electrolyte layer.

21 Claims, 11 Drawing Sheets

OXYGEN SENSOR AND METHOD OF MAKING IT

This application is a continuation-in-part of U.S. Pat. application No. 07/196,185, filed May 16, 1988, now abandoned and U.S Pat. application No. 07/282,980, filed Nov. 28, 1988, now abandoned, which is a continuation of U.S. Pat. application No. 07/029,560, filed Mar. 24, 1987, now abandoned.

BACKGROUND OF THE INVENTION

The present invention relates to an oxygen sensor that is capable of measuring the concentration of oxygen in for example, the exhaust from an internal combustion engine.

With a view to improving fuel economy and reducing emissions, feedback control of the air/fuel ratio for internal combustion engines is currently performed on the basis of measurements of the oxygen partial pressure of the exhaust from the engine. The oxygen partial pressure of the exhaust gas is measured with an oxygen sensor that employs a layer of an oxygen-ion conductive electrolyte such as a solid solution compound of zirconia or yttria. An example of this type of oxygen sensor is proposed in Unexamined Published Japanese Utility Model Application No. 100658/1985. The sensor shown in this patent has an oxygen-ion conductive solid electrolyte layer disposed in the gap between an inner and an outer electrode that are concentrically arranged in a cylindrical form. This sensor may be considered as an oxygen concentration sensor which measures a gas to be analyzed on the outer surface of the solid electrolyte layer. That is, the sensor constitutes a measuring system without introducing a reference atmosphere.

In order to ensure that atmospheric air which is used as & a reference oxygen source in the sensor described above, is introduced to make contact with the inner surface of the solid electrolyte layer without mixing with the gas to be analyzed, a so-called "green sheet" is used. The green sheet has a slit that provides an air introducing channel and must be wrapped around a core material, which may be in a bar form and which is covered with the solid electrolyte layer. The assembly of the core and the green sheet is sintered to make a product having a channel for introducing the reference atmosphere. In other words, at least two layers one being a green sheet of the solid electrolyte layer for effecting measurement of the oxygen partial pressure and the other being a green sheet that serves as a spacer and is provided with the slit described above, must be sintered after they are concentrically wound. However, considerable difficulty is involved in producing a concentric assembly of more than one green sheet without introducing any distortion. Also the required increase in the number of steps in the manufacturing process leads to a lower production rate.

Another problem with the technique described above is that the use of a bar for the core material causes an increase in the heat capacity of the oxygen sensor. In order to hold the sensor at a temperature that is suitable for the intended measurement a heater for the electrodes must have a high heat generation rating, but then the power consumption of the heater is increased while its durability is reduced.

Unexamined Published Japanese Patent Applications Nos. 125448/1980 and 36949/1985 disclose oxygen sensors that determine the oxygen partial pressure with measuring electrodes formed on the surfaces of a detecting element having a flat plate form.

However such conventional oxygen sensors having measuring electrodes formed on the surfaces of a detecting element in flat plate form have inherent directionality with respect to the direction of flow of the gas to be analyzed, and hence their outputs vary depending upon the direction of flow of the & gas of interest or the position at which the sensor is installed, thereby making it difficult to achieve proper control of the A/F ratio and other parameters on the basis of the sensor output. In order to alleviate this problem, an oxygen sensor has been proposed in Japanese Patent Application No. 66663/1986 employing a tubular detecting element.

SUMMARY OF THE INVENTION

An object, therefore, of the present invention is to provide an oxygen sensor that is easy to fabricate and has a small heat capacity.

The oxygen sensor of the invention can be summarized as a hollow cylindrical member closed at one end but open at the other to admit a reference gas. There is at least one radial through hole in the hollow cylindrical member. An oxygen-ion conductive solid electrolyte layer has at least one pair of & electrodes on its opposite sides. The electrolyte layer is wrapped around the hollow cylindrical member with the electrode on its inner side facing the through hole.

More specifically, the oxygen sensor of the present invention, which has been accomplished in order to solve the aforementioned problems of the conventional product includes a hollow cylindrical member that is open at one end and is provided with a closing wall at the other end and which has a through-hole in the side wall. An oxygen-ion conductive solid electrolyte layer shrouds the hollow cylindrical member. The hollow cylindrical member has at least one pair of electrodes on opposite sides. The electrode on the inner surface of the solid electrolyte layer is disposed in an area corresponding to the through-hole in the hollow cylindrical member.

The hollow cylindrical member in the oxygen sensor of the present invention provides a reference gas introducing channel in that the atmospheric air serving as a reference oxygen source enters the member at the open end and exits by way of the through hole to be introduced into an oxygen concentration electrochemical cell which is composed of the solid electrolyte layer and a pair of electrodes. The hollow cylindrical member may be fabricated by a suitable technique such as pressing with dies or extrusion molding. The material of the hollow cylindrical member may be selected from among ceramics, metals and other materials that do not have any significant difference in thermal expansion coefficient from the solid electrolyte layer. If the gas to be analyzed is the exhaust from an internal combustion engine that will become as hot as 600° C. or higher, ceramics are advantageously used. If a metal is used, the hollow cylindrical member must be electrically insulated from the electrode on the inner surface of the solid electrolyte layer.

The solid electrolyte layer may be formed of any material that has oxygen-ion conductivity such as $Y_2O_3$—$ZrO_2$ or $CaO$—$ZrO_2$.

The electrodes provided on opposite sides of the solid electrolyte layer may be formed of a noble metal such as platinum or a gas-permeable material that is made of a mixture of a noble metal and a ceramic powder.

The components described above may be assembled into an oxygen sensor by a variety of methods. In one method, a green sheet of solid electrolyte that has electrodes printed on opposite sides by a thick-film deposition process is wrapped around the hollow cylindrical member in such a manner that the electrode on the inner surface of the sheet is located in an area that corresponds to the through-hole in the hollow cylindrical member. The assembly is then fixed in a tubular form with a suitable jig and sintered to form a unitary member of the oxygen sensor system.

A heating element may be printed in the neighborhood of the electrode on the inner surface of the solid electrolyte layer by a thick-film deposition process. Alternatively, a heating element may be printed in the neighborhood of the electrode on the outer surface of the solid electrolyte layer by a thick-film deposition process. An advantage of providing a heating element is that an area of the solid electrolyte layer in the neighborhood of either electrode can be heated to a temperature that is suitable for the intended measurement.

The oxygen sensor of the present invention has a reference gas introducing channel that extends through the hollow cylindrical member for receiving the atmospheric air at the open end and letting it out of the member by way of the through-hole so that the air contacts the electrode on the inner surface of the solid electrolyte layer. Since the reference gas is brought into contact with the inner surface of the solid electrolyte layer while its outer surface contacts the gas to be analyzed, the partial pressure of oxygen in the gas to be analyzed can be determined by measuring the current flowing between the electrodes on opposite sides of the electrolyte layer. If this construction is employed, an oxygen sensor can be fabricated without using any green sheet having a slit for providing a reference gas introducing channel. In addition the use of a hollow cylindrical member contributes to the making of an oxygen sensor that is simple in construction and which hss a small heat capacity.

Another object of the present invention is to further reduce the directionality of such a tube-type oxygen sensor by incorporating additional structural features.

The above and other objects of the present invention are attained by an oxygen sensor that comprises a hollow tubular member and a layer of an oxygen-ion conductive solid electrolyte, the hollow tubular member being open at one end and having a closing wall at the other end, the hollow tubular member also having a plurality of through-holes that establish communication between the inner and outer surfaces of the tubular member and the layer of oxygen-ion conductive solid electrolyte surrounding the hollow tubular member and having at least two pairs of electrodes in the inner and outer surfaces thereof, the electrodes on the inner surface of the layer of solid electrolyte being disposed at positions in registry with the through-holes in the hollow tubular member. A characteristic feature of this sensor lies in the fact that the paired electrodes are spaced at substantially equal distances on the circumference of the layer of solid electrolyte.

If the number of electrode pairs is N, it suffices for the purposes of the present invention that the pairs of electrodes are spaced on the circumference of the layer of solid electrolyte at angles of $360°/N \pm 30°$, $360°/N$ being the central angle formed by two radii extending to the centers of the adjacent individual electrodes. In other words, if the deviation in the distance between adjacent electrode pairs is within 30° from the central angle, precise oxygen partial pressure measurements can be achieved irrespective of the direction of the flow of the gas to be analyzed. For instance, in order to reduce the directionality of an oxygen sensor, two electrode pairs are desirably spaced at an angle of 180° and three electrode pairs at an angle of 120°.

In the preferred embodiment, a heat generating element may be provided in the vicinity of the electrodes on the inner or outer surface of the solid electrolyte layer. This is desirable for the purpose of improVing the efficiency of heating by the heat generating element making it easily possible to heat the area in the vicinity of the electrodes to a temperature suitable for oxygen partial pressure measurements.

The hollow tubular member in the sensor of the present invention forms a reference gas introducing chamber that starts at the open end of the tubular member and passes through its interior to introduce atmospheric air as a reference oxygen source past the through-holes. This hollow tubular member can be fabricated for example, by pressing using molds or by extrusion molding. In order to prevent breakage due to thermal expansion mismatch, this hollow member may be made of a material such as a ceramic or metal that has a thermal expansion coefficient close to that of the solid electrolyte layer. If the gas to be analyzed is exhaust from an internal combustion engine, high temperatures of at least 500° C. are anticipated, and in this case ceramics are advantageously used as the material of the hollow tubular member. If a metal such as stainless steel alloy is to be used, the inside surface of the solid electrolyte layer should be insulated from the electrodes.

The solid electrolyte layer is made of an oxygen-ion conductive solid electrolyte such as $ZrO_2-Y_2O_3$ or $ZrO_2-CaO$.

The electrodes are made of a gas permeable material as may be prepared from noble metals such as platinum or mixtures thereof with a ceramic powder.

The oxygen sensor of the present invention is fabricated essentially by wrapping around the hollow tubular member a green sheet of a solid electrolyte on which electrodes are formed by a thick-film printing process. In wrapping the green sheet care should be taken so that the electrodes on the inner surface of the green sheet are registered with the throughholes in the hollow tubular members. After being wrapped around the tubular member, the green sheet is fixed in a tubular form with the aid of a jig, and the two members are fired into a unitary assembly, The oxygen sensor of the present invention has formed in its interior a reference gas introducing channel that starts at the open end of the hollow tubular member and passes through a plurality of through-holes to reach at least two electrodes the inner surface of the solid electrolyte layer. According to this construction, the inner surface of the solid electrolyte layer is in contact with a reference gas whereas the outer surface of the solid electrolyte layer is exposed to the gas to be analyzed, and the partial pressure of oxygen in the gas to be analyzed can be determined by measuring the electric current flowing between the electrodes formed on the inner and outer surfaces of the solid electrolyte layer. In addition, the paired electrodes are Spaced at substantially equal distances on the circumference of the solid electrolyte layer, which allows for exact detection of oxygen concentrations irrespective of the direction of the flow of the gas to be analyzed or the position at which the sensor is installed.

DESCRIPTION OF THE PREFERRED EMBODIMENTS

A specific first embodiment of the present invention is hereinafter described with reference to FIGS. 1 to 5, wherein the components are not shown to scale for the sake of clarity.

Figure 1:
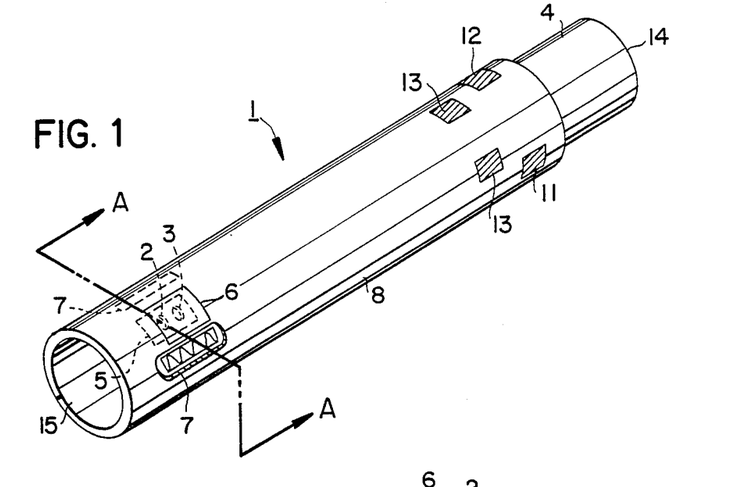
FIG. 1 is a perspective view of an oxygen sensor in accordance with a first embodiment of the present invention.

As shown in FIG. 1, the oxygen sensor according to the first embodiment of the present invention is generally indicated at 1 and is composed of a hollow cylindrical member 4 which is wrapped with a solid electrolyte layer 8. The hollow cylindrical member 4 is made of $ZrO_2$ and has through-holes 2 and 3 in its outer surface. The solid electrolyte layer 4 is provided on the inside with a reference electrode 5, and on the outside with a measuring electrode 6 and two heating elements 7. The two heating elements 7 shown in FIG. 1 are separately shown as being covered by the solid electrolyte layer 8 and in a partially exposed section in which the undulatory structure of the heater elements 7 is evident.

Figure 2:
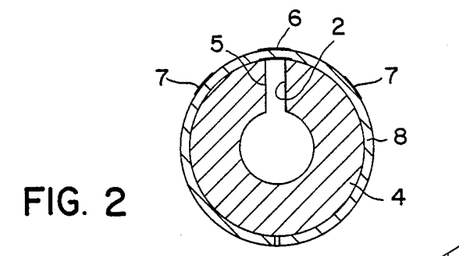
FIG. 2 is a cross section of FIG. 1 taken on the line A—A in FIG. 1.

A cross section of FIG. 1 taken on the line A—A is shown in FIG. 2, from which one can see that the reference electrode 5 is disposed in a selected area of the inner surface of the solid electrolyte layer 8 in contact with the hollow cylindrical member 4. This selected area corresponds to the through-holes 2 and 3. The measuring electrode 6 is disposed in a selected area of the outer surface of the solid electrolyte layer 8 which is opposite to and corresponds to the reference electrode 5. The heating elements 7 are provided on the outer surface of the solid electrolyte layer 8 in such a way that the measuring electrode 6 lies between them.

The inside reference electrode 5 is connected to a terminal 11 (see FIG. 1) by way of a through-hole in the solid electrolyte layer 8. The measuring electrode 6 is connected to a terminal 12 and the heating elements 7 are connected to two terminals 13.

Figure 3:
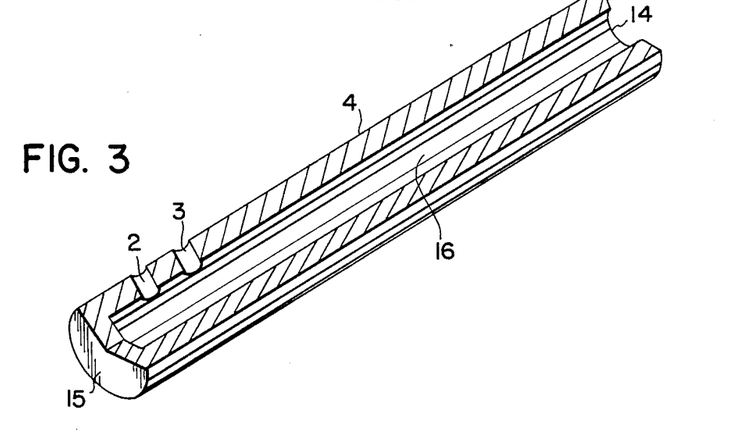
FIG. 3 is a partial fragmentary view of the hollow cylindrical member used in the oxygen sensor of FIG. 1
Figure 4:
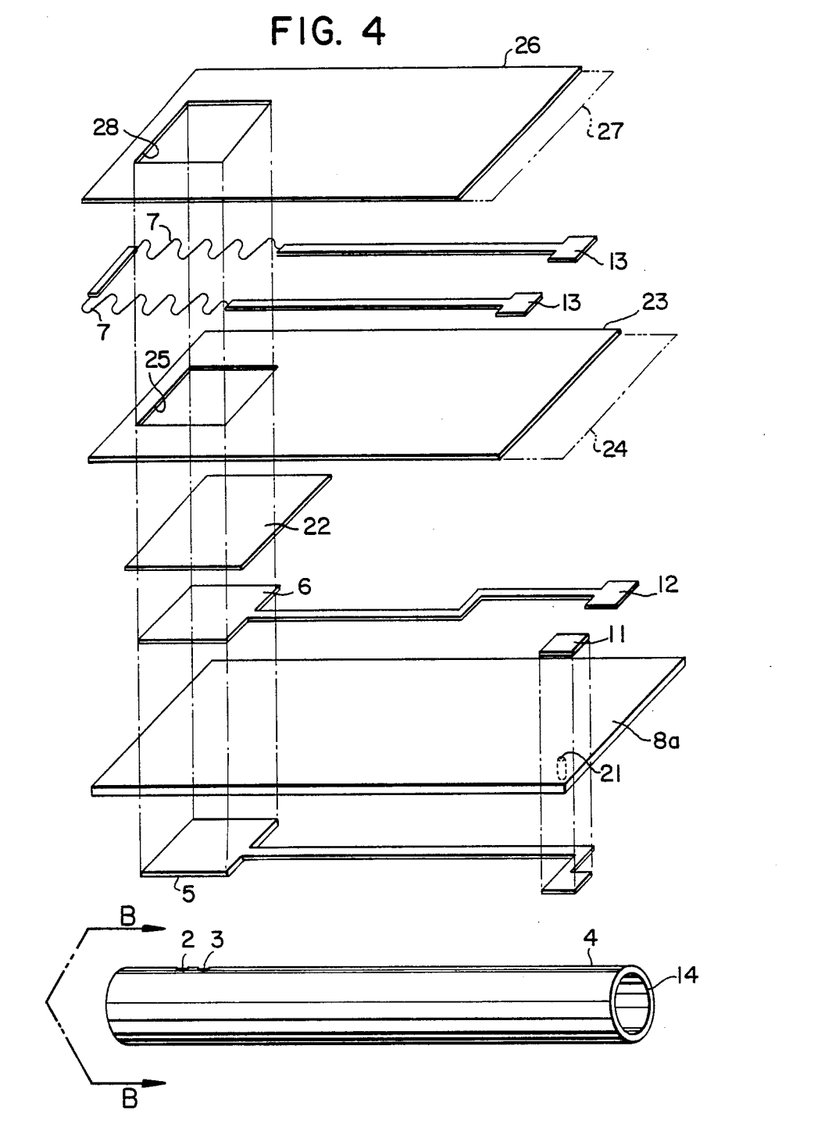
FIG. 4 shows the sensor of FIG. 1 in an unassembled state.

FIG. 4 shows the oxygen sensor of the first embodiment in unassembled state and the hollow cylindrical member 4 shown in the bottom of FIG. 4 is depicted also in FIG. 3 in cross section taken along the line B—B. As shown the hollow cylindrical member 4 has an outside diameter of 3.2 mm and an inside diameter of 1.5 mm and is open at one end 14 while it is closed at the other end with a wall 15. Two through-holes 2 and 3 each having a diameter of 1 mm are made in a selected area of the side wall which is in the neighborhood of the closing wall 15. The end opening 14 the hollow portion 16 and the through-holes 2 and 3 of the hollow cylindrical member 4 form a reference gas introducing channel in that the atmospheric air which enters at the opening 14 flows through the hollow portion 16 and exits by way of the through-holes 2 and 3. The hollow cylindrical member 4 having the construction described above can be readily produced by pressing with dies or by extrusion molding.

As shown in FIG. 4. the solid electrolyte layer 8 is formed from a green sheet 8a that is made of a powder of a solid solution compound of $Y_2O_3$ and $ZrO_2$ which is mixed with a conventional binder. A through-hole 21 through which the reference electrode 5 is connected to the terminal 11 is made at a corner of the green sheet 8a.

The reverse side of the green sheet 8a which will serve as the inner surface of the solid electrolyte layer 8 is provided with the reference electrode 5 that is formed by printing a zirconia-containing platinum layer in a thickness of 10 $\mu$m by a thick-film deposition technique.

The obverse side of the green sheet 8a which will serve as the outer surface of the solid electrolyte layer 8 is provided with the following components that are formed by a thick-film printing process. First, the reference electrode terminal 11, the measuring electrode 6 and the measuring electrode terminal 12 are formed from zirconia-containing platinum in a 10 $\mu$m thick layer. Then a protective layer 22 that is made of platinum-containing alumina and which has a thickness of 20 $\mu$m is formed on the surface of the measuring electrode 6. In the next step, an insulating layer 23 that is made of alumina and which has a thickness of 30 $\mu$m is formed on the entire surface of the green sheet 8a except for an area 24 covered by the terminals 11 and 12 and an area 25 occupied by the measuring electrode 6. Subsequently, the two heating elements 7 and heater terminals 13 each of which is made of alumina-containing platinum and has a thickness of 10 $\mu$m. are formed on the surface of the insulating layer 23. Finally, an insulation layer 26 that is made of silica-containing alumina and which has a thickness of 20 $\mu$m is formed on the entire surface of the insulating layer 23 except for an area 27 covered by the heater terminals 13 and an area 28 occupied by the measuring electrode 6.

The green sheet 8a that has been provided with the necessary parts by a thick-film printing process is then coated with a layer of zirconia paste on its reverse (inner) side and is wrapped around the hollow cylindrical member 4 such that the reference electrode 5 will be situated in an area that corresponds to the through-holes 2 and 3 in the hollow cylindrical member 4. The wrapped green sheet 8a is securely held against the hollow cylindrical member 4 by rubber pressing under vacuum, and then sintered in the atmosphere to produce an oxygen sensor which is generally indicated at 1 in FIG. 1.

Figure 5:
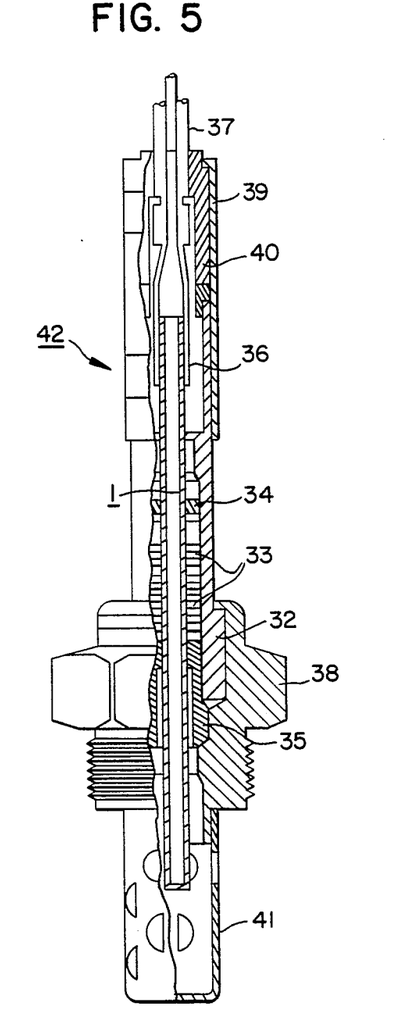
FIG. 5 is a partial fragmentary view of an oxygen detecting probe that uses the sensor of FIG. 1.

The oxygen sensor 1 thus fabricated is fixed in holder 32, shown in FIG. 5 with the aid of a filler powder 33 of carbon black, talc, etc., a packing 34 and a caulking ring 35. A terminal compressing metal fixture 36 is brazed to each of the terminals 11, 12 and 13 and a separate lead wire 37 is compressed against each of these metal fixtures. Subsequent installation of a metal frame 38, a protective casing 39, a grommet 40 and a protector 41, allowing gas flow to the measuring electrode 6 completes the assembly of an oxygen detecting probe 42.

In the oxygen sensor 1 of the first embodiment, the atmospheric air is introduced into the hollow cylindrical member 4 at the open end 14, from the upper side of FIG. 5, and flows out by way of the through-holes 2 and 3 to make contact with the reference electrode 5. Since the necessary reference gas introducing channel is provided without employing any slotted green sheet, the oxygen sensor of the present invention can be manufactured at a high production rate while involving a reduced number of steps.

In addition, the use of the hollow cylindrical member 4 contributes to a reduction in the heat capacity of the sensor. and this leads to an improvement in the thermal efficiency of the heating elements 7 and, hence, to a smaller power consumption. As a further advantage, the heating elements 7 are printed on the surface of the green sheet 8a by a thick-film deposition process, and this provides for very easy fabrication of an oxygen sensor.

A second embodiment of the present invention is hereinafter described with reference to FIG. 6. The most important feature of this embodiment is that heating elements are provided on the inner surface of a solid electrolyte layer.

Figure 6:
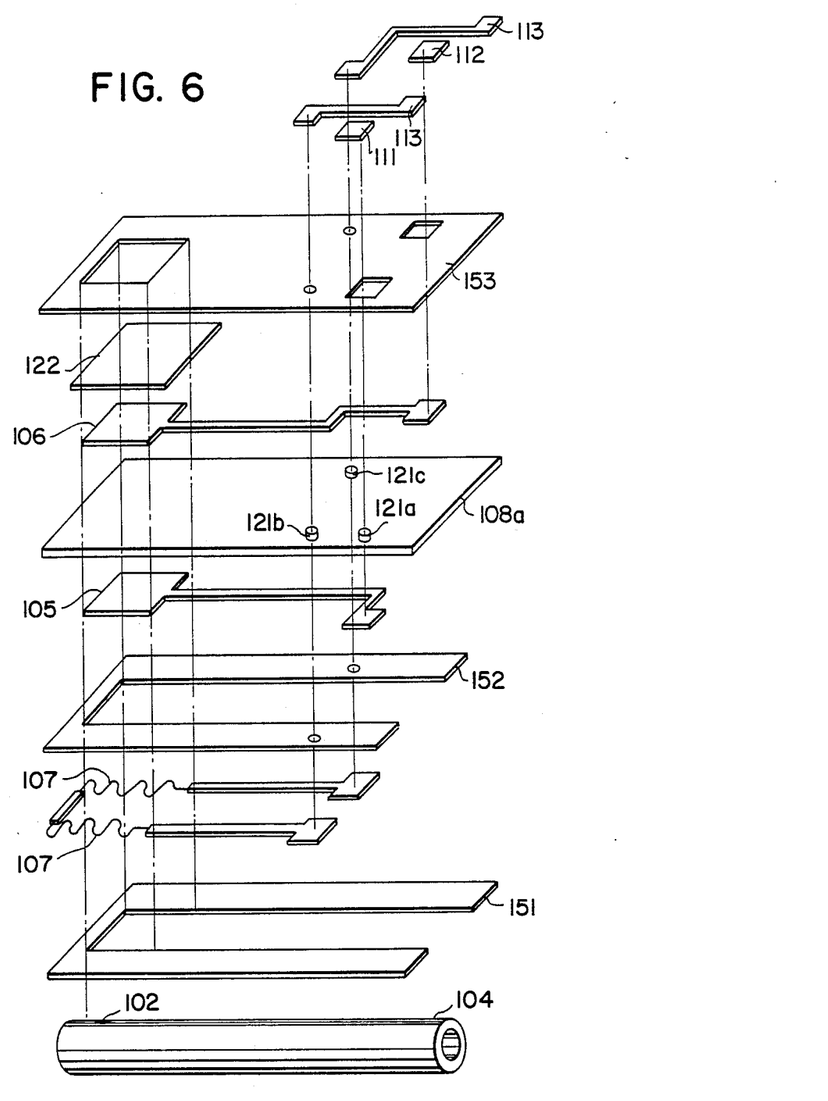
FIG. 6 shows an oxygen sensor according to a second embodiment of the present invention in an unassembled state.

As shown in FIG. 6, the reverse side of green sheet 108a which will serve as the inner surface of the solid electrolyte layer is provided by a thick-film printing process with a reference electrode 105, an insulating layer 152, heating elements 107 and an insulating layer 151, in the stated order. The obverse side of the green sheet 108 which will serve as the outer surface of the solid electrolyte layer is provided by a thick-film printing process with a measuring electrode 106, a protective layer 122, an insulating layer 153 a reference electrode terminal 111, a measuring electrode terminal 112 and heater terminals 113, in the stated order. The green sheet 108a thus provided with the necessary components is wrapped around a hollow cylindrical member 104 in such a manner that the reference electrode 105 on the green sheet 108a will be situated in an area that corresponds to a through-hole 102 made in the side wall of the hollow cylindrical member 104. Thereafter the assembly is sintered as in the first embodiment to thereby produce an oxygen sensor. The components of the sensor are made of the same materials as employed in the first embodiment.

In the second embodiment described above, the heating elements 107 are formed on the same side of the green sheet 108a as where the reference electrode 105 is provided and this enables the reference electrode to be heated with a very high efficiency to a temperature that is suitable for the intended measurement. Even if the gas to be analyzed has a low temperature. the partial pressure of oxygen in that gas can be readily measured since the measuring zone will not become too cold to achieve the measurement. An obvious advantage resulting from this feature is that if the sensor is used for measurement of the oxygen partial pressure of the exhaust from an internal combustion engine, the intended measurement can be started immediately after the engine is started.

A third embodiment of the present invention is hereinafter described with reference to FIG. 7. The main thrust of this embodiment lies in using the hollow cylindrical member of the first embodiment as a component of an air/fuel ratio sensor.

Figure 7:
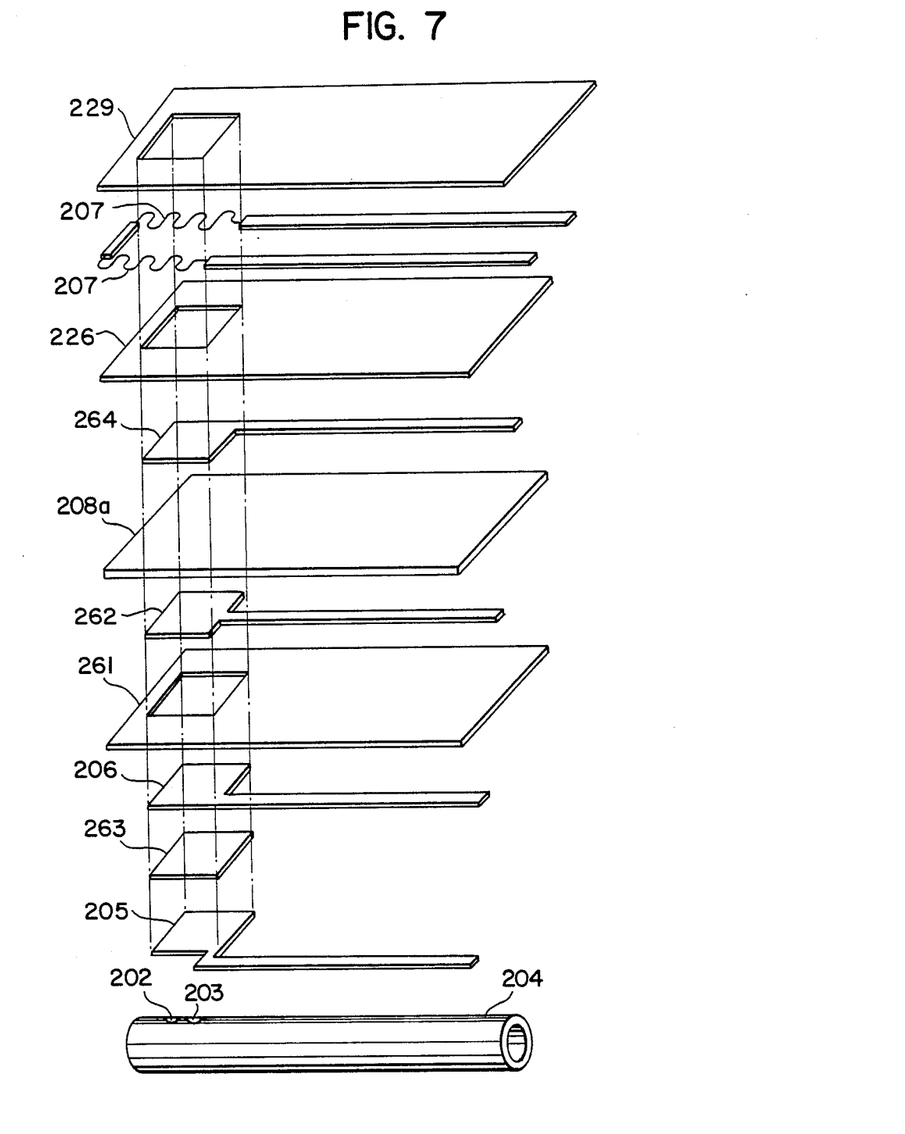
FIG. 7 shows an oxygen sensor according to a third embodiment of the present invention in an unassembled state.

As shown in FIG. 7, the reverse side of a green sheet 208a which will serve as the inner surface of the solid electrolyte layer is provided with by a thick film printing process with a second pump electrode 262, a diffusion limiting layer 261, a measuring electrode 206, another electrolyte layer o 263 and a reference electrode 205, in the stated order. The obverse side of the green sheet 208a which Will serve as the outer surface of the solid electrolyte layer is provided by a thick-film printing process with a first pump electrode 264, an insulating layer 226, heating elements 207 and an insulating layer 229, in the stated order. The green sheet 208a thus provided with the necessary components is wrapped around a hollow cylindrical member 204 as in the first embodiment and subsequently sintered in the atmosphere to produce an air/fuel ratio sensor.

In the third embodiment described above the heating elements 207 are formed on the surface of a single layer of green sheet 208a, and this provides great convenience for the manufacture of an air/fuel ratio sensor. Since the hollow cylindrical member 204 and the single layer of green sheet 208a are the two principal components, the sensor has a reduced heat capacity and this is effective in decreasing the power consumption of the heating elements 207 while increasing their durability.

A further advantage of the sensor fabricated in accordance with the third embodiment is that using the simple construction described above, an oxygen concentration electrochemical cell element can be combined with an oxygen pump element such that an air/fuel ratio signal can be detected on the basis of a measured pump current.

While three embodiments of the present invention are described above, it should be noted that the invention is in no way limited to these particular embodiments and that various modifications can be made without departing from the spirit of the invention.

The oxygen sensor of the present invention has a simple construction in that a hollow cylindrical member that is open at one end and which has a through-hole in the side wall is used as a reference gas introducing channel and in that this hollow cylindrical member is wrapped with a solid electrolyte layer. Since only one solid electrolyte layer needs to be wrapped around the hollow cylindrical member, the desired oxygen sensor can be manufactured at high production rate involving a reduced number of steps. In addition, the use of the hollow cylindrical member is effective in reducing the heat capacity of the sensor. Not only does this improve the thermal efficiency of a heating element used to activate the sensor, but also the power consumption of the heater is reduced.

The oxygen sensor of the invention offers several advantages. It is not subject to variations by a changing gas flow. Little strain is produced by the differential thermal expansion of the structural materials. Its structure is simple so that its manufacturing cost is low. No external electric source is required.

A fourth embodiment of the present invention will hereunder be described with reference to FIGS. 8 to 12. It should be noted that, for the sake of clarity, the components of the oxygen sensor are not shown to scale in these figures.

Figures 8, 9, 10:
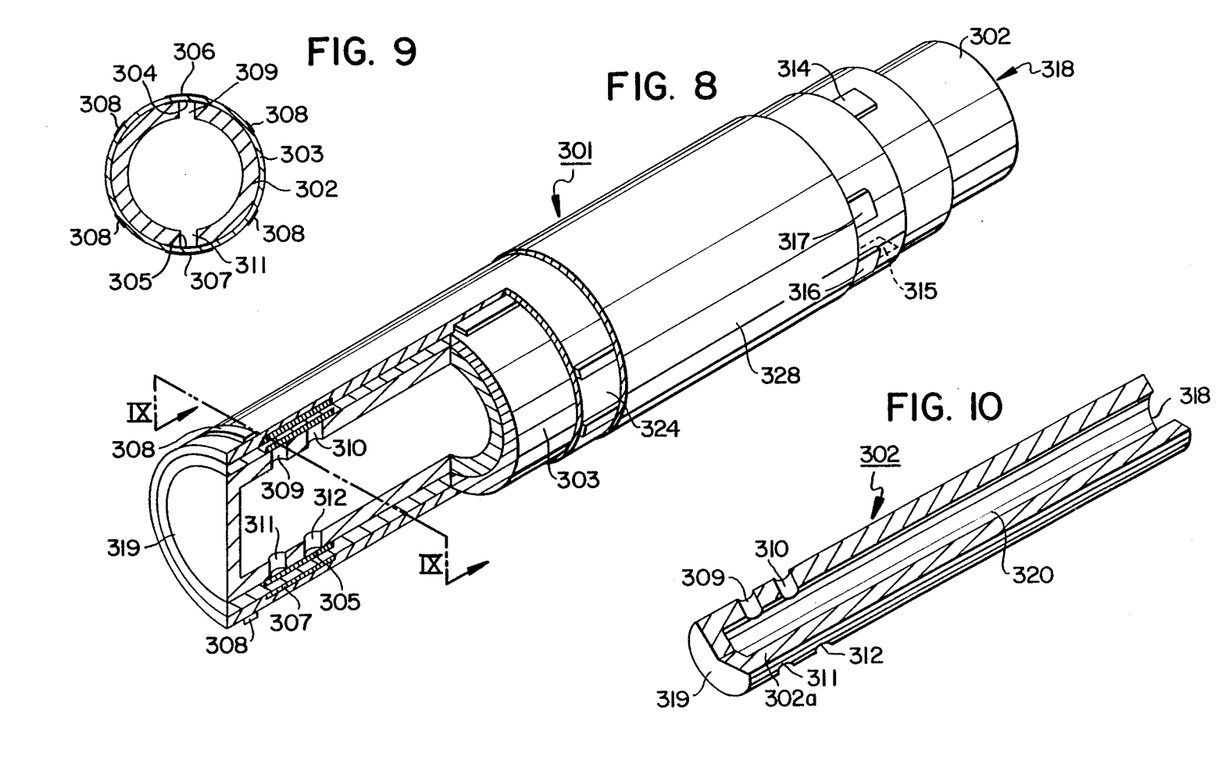
FIG. 8 is a perspective view showing an oxygen sensor with parts cut away. constructed according to a fourth embodiment of the present invention.
FIG. 9 is a cross section of the oxygen sensor of FIG. 8 taken along a line IX—IX in FIG. 8.
FIG. 10 is a partial fragmentary view of the hollow tubular member used in the sensor shown in FIG. 8.

As shown in FIG. 8, the oxygen sensor according to the fourth embodiment of the present invention is basically composed of a hollow tubular member 302 having a coating of solid electrolyte layer 303 on its surface. A first reference electrode 304 and a second reference electrode 305 are disposed on the inside surface of the solid electrolyte layer 303 and a first measuring electrode 306, a second measuring electrode 307 and a heat generating element 308 are disposed on the outside surface of the solid electrolyte 303. The hollow tubular member 302 is provided with first to fourth through-holes 309 to 312 arranged in two pairs and which establish communication with the inside and outside surfaces of the tubular member.

The first to fourth through-holes 309 to 312 are arranged in such a way that the first and second through-holes 309 and 310, which form one pair, face the third and fourth through-holes 311 and 312, which form the other pair. As shown in FIG. 9, which is a cross section of FIG. 8 taken along the line IX—IX. the first reference electrode 304 is disposed on the inner surface of the solid electrolyte layer 303, which is in contact with the hollow tubular member 302, and the first measuring electrode 306 is disposed on the outer surface of the solid electrolyte layer, with both electrodes being in registry with the first through-hole 309. In a like manner, the second reference electrode 305 and the second measuring electrode 307 are disposed in registry with the third through-hole 311. A heat generating element 308 is disposed on the outer surface of solid electrolyte layer 303.

The first and second reference electrodes 304 and 305 are connected to a reference electrode terminal 314 (see FIG. 8) via through-holes in the solid electrolyte layer 303. The first and second measuring electrodes 306 and 307 are connected to a measuring electrode terminal 315, and the heat generating element 308 to associated terminals 316 and 317.

The components of the oxygen sensor 301 and the methods for preparing them are described hereinafter. First, as shown in FIG. 10, the hollow tubular member 302 is in the form of a hollow cylinder having an outside diameter of 3.2 mm and an inside diameter of 1.5 mm, with one end 318 being open and the other end 319 being closed by a wall. In the side wall 302a near the closing wall 310 through-holes 309 to 312 arranged in two pairs and each having a diameter of 1 mm are formed in such a way that the first pair formed by the first and second through-holes 309 and 310 face the second pair formed by the third and fourth through-holes 311 and 312. As a result, a reference gas introducing channel is formed that starts at the open end 318 and extends to the first to fourth through-holes 309 to 312 through the hollow portion 320. The hollow tubular member 302 having this construction can be easily fabricated either by pressing using molds or by extrusion molding.

Figure 11:
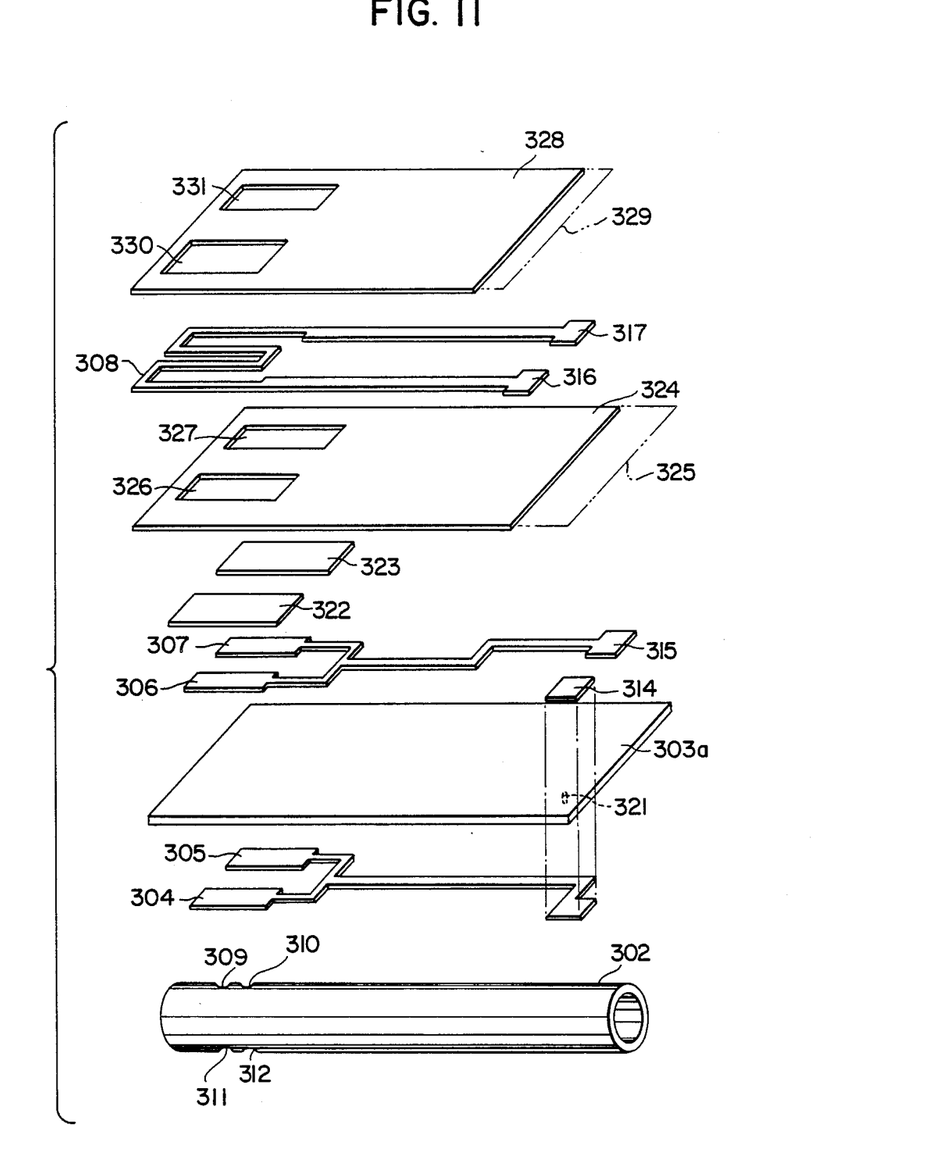
FIG. 11 is an exploded view of the oxygen sensor shown in FIG. 8.

As shown in FIG. 11, the solid electrolyte layer 303 is prepared from a green sheet 303a made of a starting powder of $ZrO_2$—$Y_2O_3$ solid solution, the particles of which are dispersed in a commonly employed binder. A through-hole 321 for establishing communication between each of the first and second reference electrodes 304 and 305 and the reference electrode terminal 314 is provided at one corner of the green sheet 303a.

The first and second reference electrodes 304 and 305 which have a thickness of 10 $\mu$m and are made of zirconia-containing platinum, are formed by a thick film process on the back side of the green sheet 303a, which is to serve as the inside surface of the solid electrolyte layer 303.

The reference electrode terminal 314 the measuring electrodes 306 and 307, and associated terminal 315 each having a thickness of 10 $\mu$m and which are made of zirconia-containing platinum, are formed by a thick-film process on the other side of the green sheet 303a, which is to serve as the outside surface of the solid electrolyte layer 303. In the next step, protective layers 322 and 323 with a thickness of 20 $\mu$m and which are made of platinum-containing alumina are formed on the surfaces of the measuring electrodes 306 and 307. respectively, by a thick-film process. The first insulating layer 324 made of alumina with a thickness of 30 $\mu$m which has windows 326 and 327 for measuring electrodes 306 and 307. respectively, is formed by a thick-film process on the surface of the green sheet 303a except for the area 325 where the electrode terminals 314 and 315 are situated. Subsequently a generally U-shaped heat generating element 308 and associated terminals 316 and 317, each being 10 $\mu$m thick and made of alumina-containing platinum, are formed by a thick film process on the surface of the first insulating layer 324 in such a way that they surround the first and second measuring electrodes 306 and 307. In the final step, the second insulating layer 328 made of silica-containing alumina. Which is 20 $\mu$m thick and which has windows 330 and 331 for measuring electrodes 306 and 307, respectively, is formed by a thick-film process on the surface of the first insulating layer 324 except for the area 329 where the electrode terminals 316 and 317 are situated.

After forming various components on the green sheet 303a by a thick-film printing process, a zirconia paste is applied to the back side of the sheet, which then is wrapped around the hollow tubular member 302 in such a way that the first reference electrode 304 is registered with the pair of through-holes 309 and 310 in the hollow tubular member 302 and the second reference electrode 305 is registered with the other pair of through-holes 311 and 312. The green sheet 303a is firmly secured to the hollow tubular member 302 by rubber pressing under vacuum and the assembly is fired in atmospheric air to produce an oxygen sensor of the type shown in FIG. 8.

Figure 12:
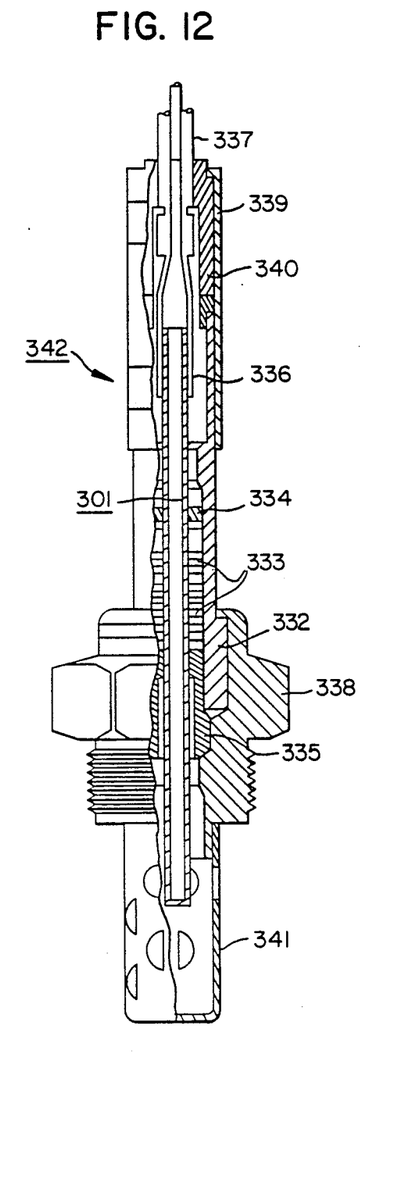
FIG. 12 is a partial fragmentary view of an oxygen detecting probe incorporating the sensor shown in FIG. 8.

The oxygen sensor 301 thus fabricated is fixed in a holder 332, as shown in FIG. 12. with the aid of a filler powder 333 such as carbon graphite or talc, a packing 334 and a caulking ring 335. A compression terminal fixture 336 is brazed to each of the terminals in the sensor and a lead 337 is also attached to the fixture 336. Thereafter, a shell 338, a protective sheath 330, a grommet 340 and a protector 341 are installed to thus provide an oxygen detecting probe 342.

The oxygen sensor 301 of the above embodiment offers the following advantages Since the electrode pair composed of the first reference electrode 304 and the first measuring electrode 306 is disposed facing the electrode pair of the second reference electrode 305 and the second measuring electrode 307, the output of the sensor 301 is less sensitive to the direction of flow of the gas to be analyzed. This ensures high precision of measurements irrespective of the position at which the sensor is installed.

In the fourth embodiment of the present invention described above, two electrode pairs are spaced apart by an angle of 180° so that they face each other diametrically. According to this arrangement, the partial pressure of oxygen in the gas to be analyzed can be precisely measured even if the flow of direction of that gas is not perpendicular to the electrode surfaces. The directionality of the oxygen sensor can also be reduced by spacing three electrode pairs at intervals of 120° or four electrode pairs at intervals of 90°.

In some instances, electrode parrs cannot be spaced equidistantly as specified above, but even in such a case the directionality of the sensor can be reduced satisfactorily if the deviation is not greater than about 30°. In other words, an oxygen sensor with reduced directionality can be realized by spacing paired electrodes on the circumference of the solid electrolyte layer at angles of $360°/N \pm 30°$, where N is the number or electrode pairs, $360°/N$ being the central angle formed by two radii extending to the centers of adjacent individual electrodes.

Compared with a conventional oxygen sensor in plate form, the sensor of the present invention which makes use of a thin-walled hollow tubular member 302 has the advantage of a sufficiently reduced heat capacity to achieve a significant improvement in the thermal efficiency of the heat generating element 308 thereby leading to reduced power consumption. In addition the sensor of the present invention can be fabricated very easily since the heat generating element 308 is formed on the surface of a green sheet 303a by a thick-film printing process.

The following experiment was conducted in order to verify these advantages of the oxygen sensor according to the fourth embodiment of the present invention.

EXPERIMENT

Figure 13:
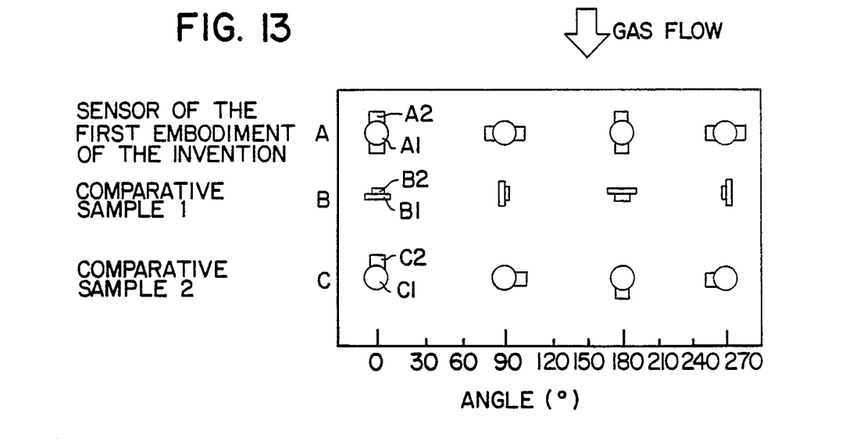
FIG. 13 is a diagram showing various mounting directions of electrodes in oxygen sensors with respect to the direction of gas flow.

An experimental apparatus using an automotive engine with a displacement of two liters was set up, and A/F ratio feedback control was exercised on the basis of the output of oxygen sensor in such a way that gasoline and air were mixed and combusted at the stoichiometric ratio ($\lambda = 1$). In this experiment, three oxygen sensors A, B and C were tested. Sensor A was designed in accordance with the fourth embodiment of the present invention which, as shown in FIG. 13, had two diametrically opposed electrodes A2 on the surface of a cylinder A1. Sensor B had an electrode B2 on the surface of a conventional tubular substrate B1 (comparative sample 1). Sensor C had a single electrode C2 on one side of a cylinder C1. The experiment was carried out by investigating the A/F ratio characteristics of the engine with the electrode position of each sensor being varied by an increment of 30° with respect to the direction of flow of the gas to be analyzed.

Figure 14:
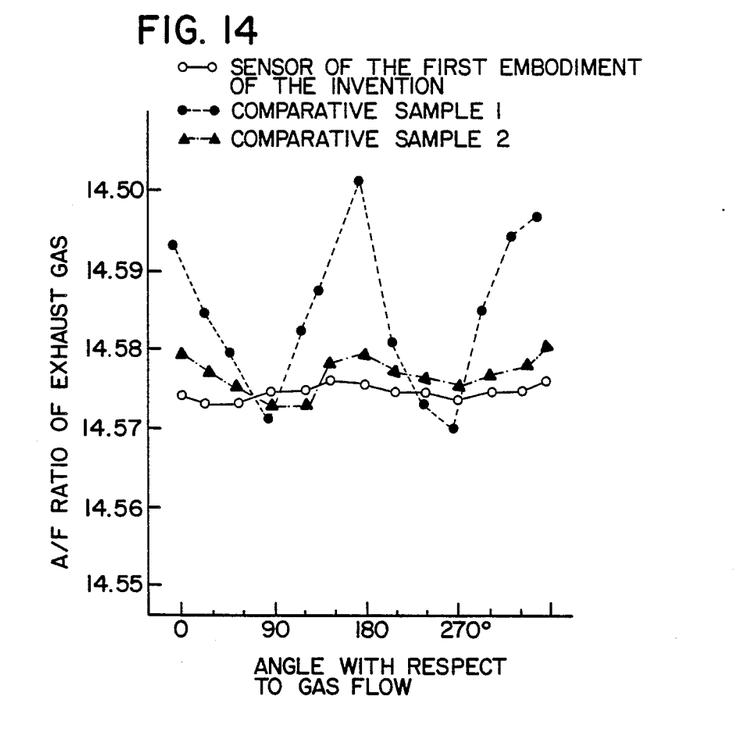
FIG. 14 is a graph showing the effectiveness of the oxygen sensor according to the fourth embodiment of the present invention.

The results of the experiment: are shown by the graph of FIG. 14. from which it can be seen that comparative sample 2 in plate form caused marked variation on the A/F ratio of the exhaust gas as the electrode position relative to the direction of flow was changed, whereas sensor A fabricated according to the fourth embodiment of the present invention was little sensitive to the direction of gas flow. Comparative sample 2 in cylindrical form was superior to comparative sample 1 but not as good as sensor A which was less sensitive to the direction of gas flow.

A fifth embodiment of the present invention will be described hereinafter with reference to FIG. 15. The fifth embodiment differs from the fourth embodiment in that a heat generating element is formed on the inner surface, rather than the outer surface, of the solid electrolyte layer.

Figure 15:
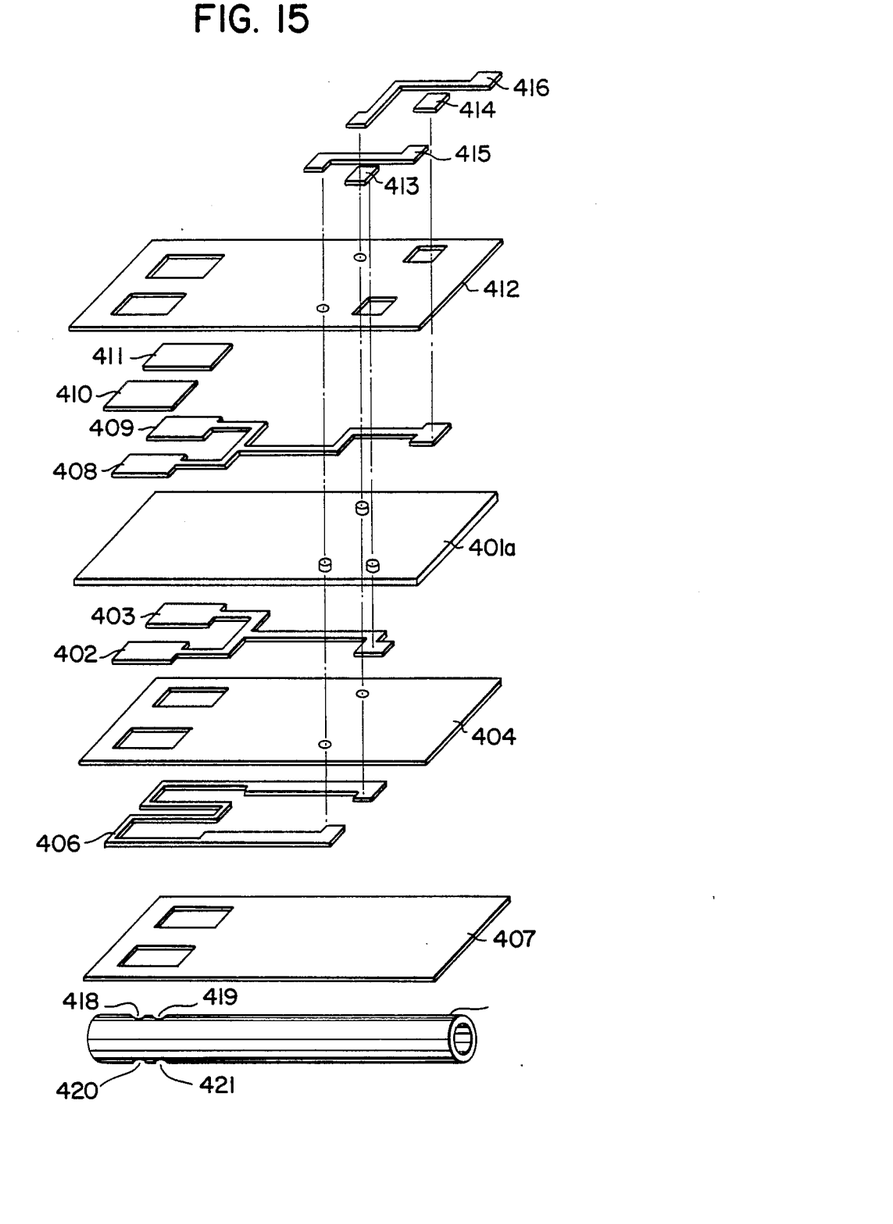
FIG. 15 is an exploded view of an oxygen sensor according to a fifth embodiment of the present invention.

As shown in FIG. 15. a pair of reference electrodes 402 and 403. a first insulating layer 404, a heat generating element 406 and a second insulating layer 407 are formed in the stated order by a thick-film process on the rear side of a green sheet 401a, which is to serve as the inner surface of the solid electrolyte layer. A pair of measuring electrodes 408 and 409, a pair of protective layers 410 and 411, a third insulating layer 412, a reference electrode terminal 413 a measuring electrode terminal 414 and heat generating element terminals 415 an 416 are formed in the stated order by a thickfilm process on the other side of the green sheet 401a, which is to serve as the outer surface of the solid electrolyte layer. The green sheet 401a is then wrapped around a hollow tubular member 417 in such a way that the reference electrode 402 is registered with the pair of through-holes 418 and 419 in the hollow tubular member 417 and the second reference electrode 403 is registered with the other pair of through-holes 420 and 421. The assembly is fired as in the first embodiment, thereby producing an oxygen sensor. The individual components of the sensor are made of the same materials as those employed in the sensor of the fourth embodiment.

In the oxygen sensor of the fifth embodiment, the heat generating element 406 is formed by a thick-film process on the same side of the green sheet.403a as that where the reference electrodes 402 and 403 are provided. Thus, these electrodes can be heated very efficiently to a temperature suitable for measurement purposes. This offers a particular advantage for the case where the partial pressure of oxygen in a cold gas is to be analyzed because the measuring portion will not be too cold to properly perform the desired measurement. Therefore, if this oxYgen sensor is used in the determination of the partial pressure of oxygen in the exhaust from an automobile, a measurement can be immediately commenced after the engine is started.

A sixth embodiment of the present invention will be described hereinafter with reference to FIG. 16. The sixth embodiment is characterized in that the hollow tubular member 302 described in connection with the fifth embodiment is applied to an A/F ratio sensor equipped with an oxygen pump element.

Figure 16:
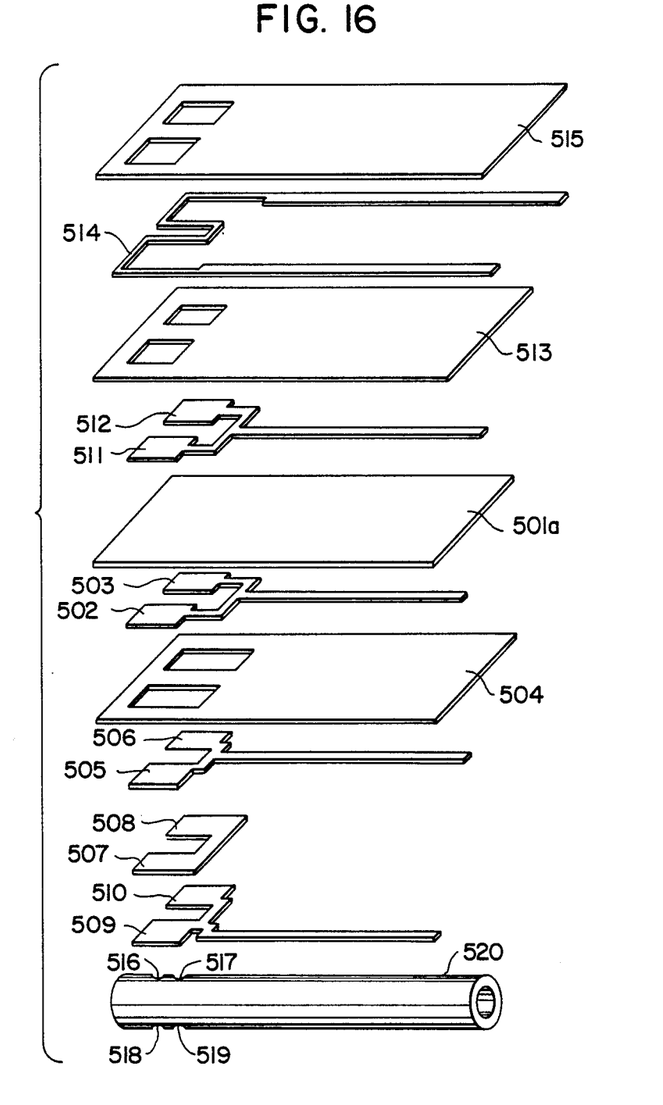
FIG. 16 is an exploded view of an oxygen sensor according to a sixth embodiment of the present invention.

As shown in FIG. 16, second pump electrodes 502, 503, a diffusion limiting layer 504, measuring electrodes 505, 506 solid electrolyte layers 507, 508, and reference electrodes 509 and 510 are formed in the stated order by a thick-film process on the rear side of a green sheet 501a, which is to serve as the inner surface of the solid electrolyte layer. First pump electrodes 511, 512, a first insulating layer 513, a heat generating element 514, and a second insulating layer 515 are formed in the stated order by a thick-film process on the other side of the green sheet 501a, which is to serve as the outer surface of the solid electrolyte layer. The green sheet 501a is then wrapped around a hollow tubular member 520 in such a manner as to attain registry with through-holes 516 to 519 arranged as in the fourth embodiment. The assembly is subsequently fired in atmospheric air to produce an A/F ratio sensor.

Compared with an A/F ratio sensor having individual elements and other components in plate form superposed one on top of another, the sensor equipped with an oxygen pump element in accordance with the sixth embodiment of the present invention is very easy to fabricate and requires only a simple combination of the oxygen pump element with an oxygen concentration electrochemical cell for the purpose of producing an A/F ratio signal on the basis of the measured pump current. In addition, being composed of the hollow tubular member 520 and the single layer of green sheet 501a, the sensor has a smaller heat capacity. Hence, not only is the power consumption of the heat generating element 514 reduced, but also its durability is improved.

As described above, the oxygen sensor of the present invention has electrode pairs spaced at substantially equal distances on the circumferences of a cylindrical solid electrolyte layer, whereby the concentration of oxygen in the gas to be analyzed can be detected precisely, irrespective of the direction of gas flow or the position at which the sensor is installed. In addition, the use of a hollow tubular member reduces the heat capacity of the sensor, which contributes to reduced power consumption of a heat generating element while enhancing its durability.

What is claimed is:

1. A method for forming an oxygen sensor comprising the steps of:
providing a hollow cylindrical member having a first open axial end and a second closed axial end, and having at least one through-hole formed in a side wall thereof;
forming first and second electrodes on opposite sides of an oxygen-ion conductive green sheet;
wrapping said green sheet with said electrodes around said cylindrical member with a one of said electrodes on a side of said green sheet adjacent said cylindrical member overlying said through hole; and
solidifying and fixing said green sheet to said cylindrical member.

2. The method for forming an oxygen sensor of claim 1. further comprising the step of, prior to said step of wrapping said green sheet around said cylindrical member, forming a heating element on one side of said green sheet.

3. The method for forming an oxygen sensor of claim 2, wherein said heating element is on said side of said green sheet adjacent said cylindrical member.

4. The method for forming an oxygen sensor of claim 3, wherein said heating element is on a side of said green sheet opposite said side adjacent said cylindrical member.

5. The method for forming an oxygen sensor of claim 2. further comprising the step of forming an insulating layer between said heating element and said green sheet.

6. The method for forming an oxygen sensor of claim 1 wherein said step of solidifying and fixing said green sheet to said cylindrical member comprises sintering.

7. The method for forming an oxygen sensor of claim 1. further comprising the step of. prior to said step of wrapping said green sheet around said cylindrical member, coating a predetermined portion of said green sheet with a layer of a zirconia paste, and wherein said step of solidifying and fixing said green sheet to said cylindrical member comprises rubber pressing said green sheet against said cylindrical member under vacuum and then sintering said green sheet in an atmosphere.

8. The method for forming an oxygen sensor of claim 1, wherein said green sheet is formed of a powder of a solid solution compound of $Y_2O_3$ and $ZrO_2$ mixed with a binder.

9. The method for forming an oxygen sensor of claim 1. wherein said step of forming said first and second electrodes comprises forming said electrodes with a thick-film printing process.

10. The method for forming an oxygen sensor of claim 9. wherein said electrodes are formed of zirconia-containing platinum.

11. The method for forming an oxygen sensor of claim 1, further comprising the step of mounting said hollow cylindrical member and said oxygen sensing member such that an outer surface of said oxygen sensing member is exposed to an atmosphere of a gas to be measured and an interior of said hollow cylindrical member is exposed to a reference gas.

12. An oxygen sensor comprising, a hollow tubular member and a layer of an oxygen-ion conductive solid electrolyte, said hollow tubular member being open at one end and having a plurality of through-holes that establish communication between inner and outer surfaces of said, tubular member, said layer of an oxygen ion conductive solid electrolyte surrounding said hollow tubular member and having at least two pairs of electrodes on inner and outer surfaces thereof the electrodes on the inner surface of said layer of solid electrolyte being disposed at positions in registry with the through-holes in said hollow tubular member, said electrode pairs being spaced at angles of $360°/N \pm 30°$ on the circumference of said layer of solid electrolyte, where N is the number of electrode pairs and $360°/N$ is a central angle formed by two radii extending to centers of adjacent ones of said electrodes.

13. The oxygen sensor according to claim 12, wherein said layer of solid electrolyte comprises a heat generating element on an inner surface thereof.

14. The oxygen sensor according to claim 12, wherein said layer of solid electrolyte comprises a heat generating element on an outer surface thereof.

15. The oxygen sensor according to claim 12, wherein said electrodes on said inner surface of said conductive solid electrolyte comprise interconnected reference electrodes.

16. The oxygen sensor according to claim 12, wherein said electrodes on said outer surface of said conductive solid electrolyte comprise interconnected measuring electrodes.

17. The oxygen sensor according to claim 12, wherein said hollow tubular member is made of a ceramic material.

18. The oxygen sensor according to claim 12, wherein said layer of solid electrolyte is made of material selected from the group consisting of $ZrO_2$—$Y_2O_3$ and $ZrO_2$—$CaO$.

19. The oxygen sensor according to claim 12, wherein said electrodes are made of a gas permeable material prepared from a mixture of at least one noble metal and a ceramic powder.

20. The oxygen sensor according to claim 12, wherein said at least one noble metal comprises platinum.

21. The oxygen sensor according to claim 12 wherein said layer of solid electrolyte is formed by wrapping a green sheet of a solid electrolyte material on which said electrodes are formed in advance around said hollow tubular member and firing said green sheet member together with said hollow tubular member.

* * * * *